United States Patent
Caers et al.

(10) Patent No.: US 7,582,802 B2
(45) Date of Patent: Sep. 1, 2009

(54) PROPYLENE HYDROFORMYLATION

(75) Inventors: Raphael Frans Caers, Edegem (BE); Hubertus Joseph Beckers, Keerbergen (BE); Eddy Theophyle Andrea Van Driessche, Eeklo (BE); Luc Roger Marc Martens, Meise (BE); John Stephen Godsmark, Grez Doiceau (BE); John Richard Shutt, Merchtem (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/591,306

(22) PCT Filed: Jan. 28, 2005

(86) PCT No.: PCT/EP2005/000946

§ 371 (c)(1), (2), (4) Date: Jun. 6, 2007

(87) PCT Pub. No.: WO2005/095547

PCT Pub. Date: Oct. 13, 2005

(65) Prior Publication Data

US 2007/0282133 A1 Dec. 6, 2007

(51) Int. Cl.
C07C 45/50 (2006.01)
(52) U.S. Cl. .................................. 568/451; 568/454
(58) Field of Classification Search ................ 568/451, 568/454; 585/327, 640
See application file for complete search history.

(56) References Cited

U.S. PATENT DOCUMENTS

| 4,262,142 | A | | 4/1981 | Sherman, Jr. et al. |
| 5,600,017 | A | | 2/1997 | Kiss et al. |
| 5,675,041 | A | | 10/1997 | Kiss et al. |
| 5,714,662 | A | * | 2/1998 | Vora et al. .................. 585/640 |
| 5,808,168 | A | * | 9/1998 | Bahrmann et al. .......... 568/454 |
| 5,960,643 | A | | 10/1999 | Kuechler et al. |
| 6,875,899 | B2 | * | 4/2005 | Martens et al. ............. 585/327 |
| 2002/0103406 | A1 | | 8/2002 | Mathys et al. |
| 2003/0045761 | A1 | | 3/2003 | Kuechler et al. |
| 2003/0187313 | A1 | | 10/2003 | Wang et al. |
| 2004/0254416 | A1 | | 12/2004 | Risch et al. |

FOREIGN PATENT DOCUMENTS

| WO | WO 96/22264 | 7/1996 |
| WO | WO 96/22265 | 7/1996 |
| WO | WO 96/22268 | 7/1996 |
| WO | WO 02/06188 | 1/2002 |

OTHER PUBLICATIONS

Beller et al., "Progress in hydroformylation and carbonylation," Journal of Molecular Catalysis, A, Chemical, vol. 104, 1995, pp. 17-85.

* cited by examiner

*Primary Examiner*—Sikarl A Witherspoon
(74) *Attorney, Agent, or Firm*—Andrew B. Griffis

(57) ABSTRACT

Propylene streams obtained by the conversion of oxygenates to olefins are used as feeds for hydroformylation. The streams may contain measurable amounts of dimethyl ether without adversely impacting the hydroformylation.

14 Claims, 7 Drawing Sheets

PROPYLENE HYDROFORMYLATION

CROSS REFERENCE TO RELATED PATENT APPLICATIONS

This application is a national stage filing of International Patent Cooperation Treaty Application No. PCT/EP2005/000946 filed Jan. 28, 2005, which claims priority from U.S. Ser. No. 10/805,983 filed Mar. 22, 2004, the disclosure of which is fully incorporated herein by reference.

FIELD OF THE INVENTION

This invention relates to hydroformylation of olefin streams to make hydroformylated products. In particular, this invention relates to the hydroformylation of a propylene containing stream obtained from the production of olefins from oxygenates. More particularly it is concerned with the hydroformylation of such streams that contain a very low amount of sulfur and/or nitrogen and/or chlorine, and a non-toxic amount of dimethyl ether.

BACKGROUND OF THE INVENTION

Hydroformylation involves reacting olefins with carbon monoxide and hydrogen using a hydroformylation catalyst. The product of the reaction process is one or more aldehydes, and perhaps certain aldehyde derivatives depending upon the reaction process. Derivatives of aldehydes include alcohols, acids, and polyols.

Olefins that are used to produce aldehyde products are typically made by cracking petroleum feedstocks, i.e., producing low molecular weight hydrocarbons from high molecular weight hydrocarbons. Cracking of petroleum feedstocks can be accomplished catalytically or non-catalytically.

The production of hydroformylated products from an olefin stream made by cracking or oxygenate conversion processes can be negatively impacted as a result of undesirable by-products coming into contact with hydroformylation catalysts. Such by-products can cause reduced efficiency in the recovery of useful hydroformylation products or can cause the formation of lower quality derivative products.

Traditional industrial olefin feeds contain impurities such as sulphur and the removal of undesirable by-products from an olefin stream can be quite difficult. For example the removal of sulfur, nitrogen and chlorine from cracked hydrocarbon streams; or the removal of dimethyl ether (DME) from $C_4$ or $C_5$ raffinate recovered from a methyl tertiary butyl ether (MTBE) or a tertiary amyl methyl ether (TAME) unit; or the removal of oxygenate by-products, including dimethyl ether, from an oxygenate to olefins unit can require a significant amount of olefin feed pretreatment. It is, therefore, desirable to find methods of hydroformylating olefin compositions which do not require extensive pretreatment of the olefin feed to remove contaminants.

SUMMARY OF THE INVENTION

This invention is concerned with a method comprising hydroformylating a stream that is rich in propylene which has been obtained from the product produced in the conversion of oxygenates to olefins. A particular benefit of the invention is that the stream is low in sulfur, nitrogen and chlorine and does not require rigorous purification. Furthermore the stream may be hydroformylated even if it contains a non-toxic amount of dimethyl ether. The invention is also concerned with a new propylene stream that is particularly useful in this method.

According to an aspect of the invention there is provided a method of making a hydroformylated product comprising contacting an oxygenate with a molecular sieve catalyst to form an olefin composition; separating a propylene containing stream from the olefin composition and contacting the propylene containing stream with a rhodium hydroformylation catalyst to form a hydroformylated product.

In a preferred embodiment of the method, the propylene containing stream contains at least 50 wt %, preferably at least 60 wt %, and more preferably at least 96 wt % propylene. Higher concentrations still of propylene are desirable for commercial reasons; thus in the method that makes use of the higher concentration propylene containing stream, the stream contains at least 97 mole % of propylene, more preferably at least 97.5 mole %, most preferably at least 98 mole %, at least 99 mole %, at least 99.5 mole % or even at least 99.9 mole % of propylene.

In another embodiment the method of the invention produces and makes use of a stream containing at least 50 wt % propylene, not greater than 10 ppb by weight of sulfur calculated on an atomic basis, and at least 100 ppb by weight of dimethyl ether (DME).

In yet another aspect the invention provides for the hydroformylation of a stream that contains at least 96 mole % of propylene, less than 50 ppb by weight of sulfur, nitrogen or chlorine, on an atomic weight basis, and more than 100 ppb by weight of dimethyl ether, the balance of the stream being primarily propane.

The propylene containing stream separated during performance of the method of the invention may be a propylene containing stream that contains from 100 ppb by weight DME to 50000 ppm by weight DME, preferably from 100 wppb DME to 5000 wppm DME. In a further embodiment the stream produced according to the method contains form 2.5 to 25000 ppm by volume of DME.

BRIEF DESCRIPTION OF THE DRAWINGS

One aspect of the invention is illustrated by FIG. 1, which is a flow diagram showing a typical way of hydroformylating a propylene containing stream. It is further discussed in Example 1.

DETAILED DESCRIPTION OF THE INVENTION

Figure 1:
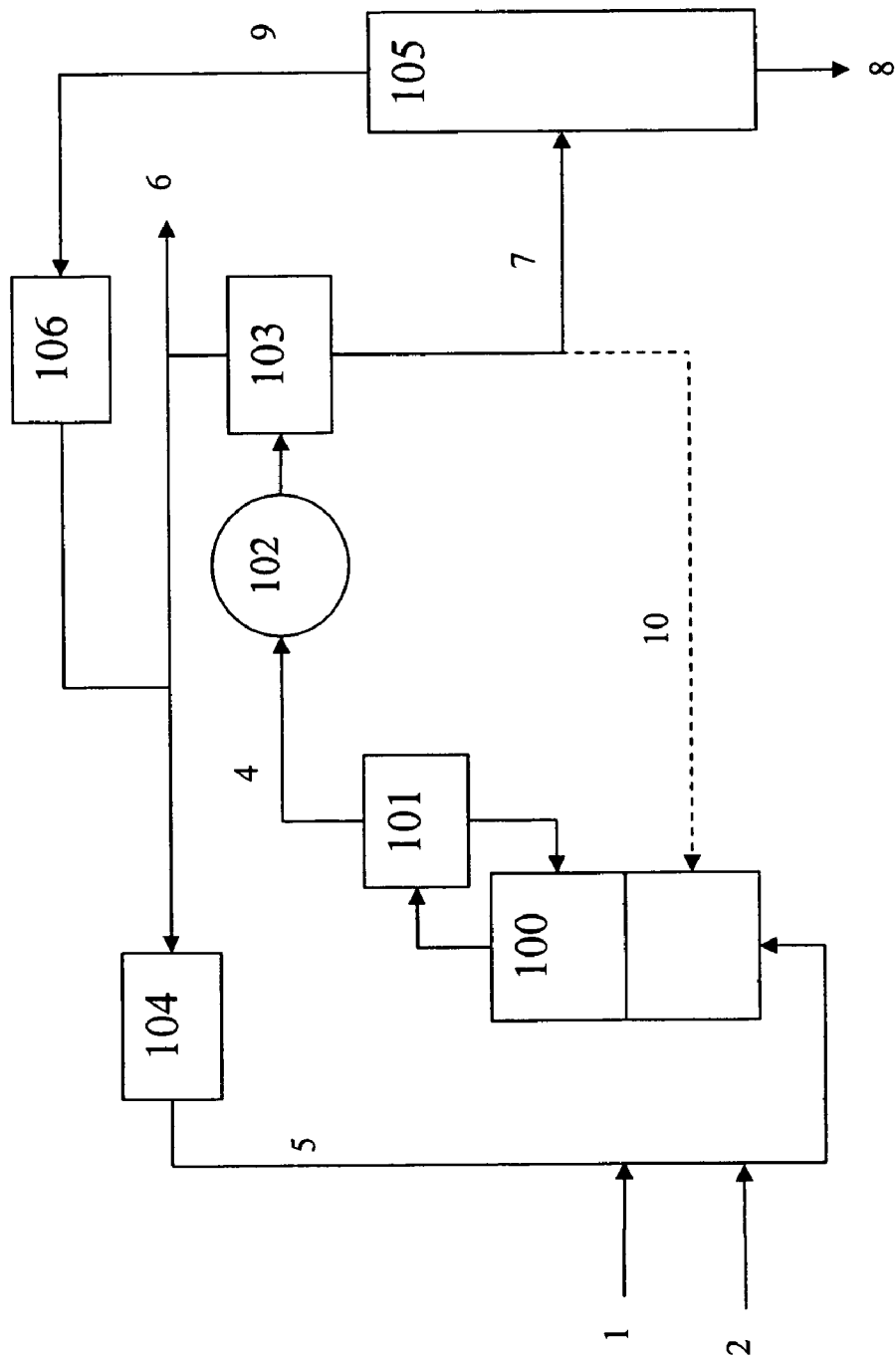

This invention is directed to hydroformylation of a propylene containing stream that is derived from the conversion of oxygenates to olefins.

The method is accomplished by separating a desired propylene containing fraction from an olefin product produced in an oxygenate to olefins reaction process, and contacting the separated propylene containing stream with a rhodium hydroformylation catalyst to form a hydroformylated product. This method has the benefit that extensive pretreatment of the olefin feed may not be required.

The appropriate propylene containing fraction preferably contains a very low concentration of sulfur and/or nitrogen and/or chlorine. However, it has been found that the fraction may contain a non-toxic quantity of dimethyl ether, even though it is known that only a small amount of dimethyl ether generally acts as a poison to many of the catalysts that are frequently used to further process the olefins in the separated propylene streams separated from oxygenate to olefins product streams. For example, metallocene catalysts which are used to polymerize ethylene and propylene are highly sensitive to sulfur, nitrogen, chlorine and dimethyl ether.

It is important in this invention, that the propylene containing fraction be separated from the olefin product of the oxygenate to olefins reaction so as to contain a major amount of propylene and a lesser amount of ethylene and/or butenes. This type of separation, which can be accomplished using conventional means, will tend to concentrate dimethyl ether, which is likely to be present in the olefin product of the oxygenate to olefin process, in the propylene/propane fraction.

Accordingly the present invention also provides a propylene composition comprising propylene, less than 5 weight percent ethylene, and from greater than 2 volume ppm to 50000 volume ppm dimethyl ether.

Preferably the propylene composition comprises less than 4 weight percent, more preferably less than 1 weight percent ethylene. In particular progressively preferred embodiments the ethylene content of the composition is less than 100 volume vppm, less than 15 vppm, less than 10 vppm.

In one preferred embodiment, the propylene composition contains at least 50 weight percent propylene, preferably at least 96 weight percent of propylene, more preferably greater than 97 weight percent propylene, and particularly preferably greater than 99 weight percent propylene.

The composition is required to contain more than 2 vppm dimethyl ether (DME), up to a maximum of 50000 vppm DME. Preferably the DME content is from 2.5 to 25000 vppm, more preferably from 5 to 5000 vppm. Such compositions have been found to be obtainable by processes for the conversion of oxygenates to olefins. As described elsewhere herein, such conversion processes may result in propylene containing compositions that additionally contain DME.

Preferably the propylene compositions will contain not greater than 10 ppb by weight of sulphur, calculated on an atomic basis.

With reference to the above-stated volume ppm units, it is known that concentrations expressed in volume fractions are the same as in molar fractions. When converting a concentration that is expressed in volume fraction into weight fraction, a component of a composition having a molecular weight below the average molecular weight of the total composition will have a weight fraction that is a lower number than its volume fraction. Conversely, for a component having a molecular weight above the average molecular weight of the total composition, a concentration expressed in volume fraction will become a higher number when converted to a weight fraction.

US 2005/0033013-A is concerned with propylene-containing compositions that are preferably suitable for polymerization and are preferably derived from an oxygenate to olefin reaction system such as a methanol to olefin reaction system. The target compositions of the earlier application comprise at least 95 volume percent propylene and from 0.5 to 2 vppm dimethyl ether. Thus the earlier application does not specifically disclose, as its claimed compositions, propylene compositions containing more than 2 vppm DME. However, that application discloses that the target composition may be obtained by performing an oxygenate to olefin reaction that results in an "initial effluent stream" comprising DME, ethane, ethylene and propylene. Various DME contents of such stream are disclosed, including greater than 1.0, 2.0 or 3.0 weight percent. The stream is required to contain ethylene, but the only teachings concerning the amount of ethylene contained in the initial effluent stream are variously: at least 25 weight percent, 25-75 wt %, 30-60 wt % and 35-50 wt %. The earlier application goes on to state that in terms of lower range limitations the stream contains optionally at least about 5, 10 or 20 weight percent ethylene. Therefore, there is no teaching in said earlier application of a propylene composition that contains, in addition to propylene and >2 to 50000 vppm DME, less than 5 wt % (or less than 4 wt %) ethylene.

We have found that when such a separated propylene containing stream is used as a feed to a hydroformylation process which uses a rhodium catalyst, particularly a low pressure rhodium process, the dimethyl ether will not significantly affect the catalytic activity of the catalyst and the use of this propylene composition overcomes the traditional need to remove dimethyl ether from such materials.

The amount of dimethyl ether (DME) in the propylene stream may be measured by gas chromatography (GC), using a flame ionization detector (FID) or preferably a thermal conductivity detector (TCD) detection system because the latter gives a higher response signal for DME. GC mass spectrometry (GCMS) may be used to detect very low levels of DME.

The propylene containing stream is separated from the ethylene containing fraction typically in a de-ethaniser tower. Separation of the propylene containing stream from the butene containing fraction is typically done in a depropaniser tower. These two towers can be in any order, and both process sequences are known and practised in commerce. Other process steps for treating the stream may be disposed upstream of the first tower, and/or in between the two towers, and/or downstream of the second tower. Optionally, the propylene containing stream is further concentrated by a superfractionation treatment as shown in FIG. 2.

Figure 2:
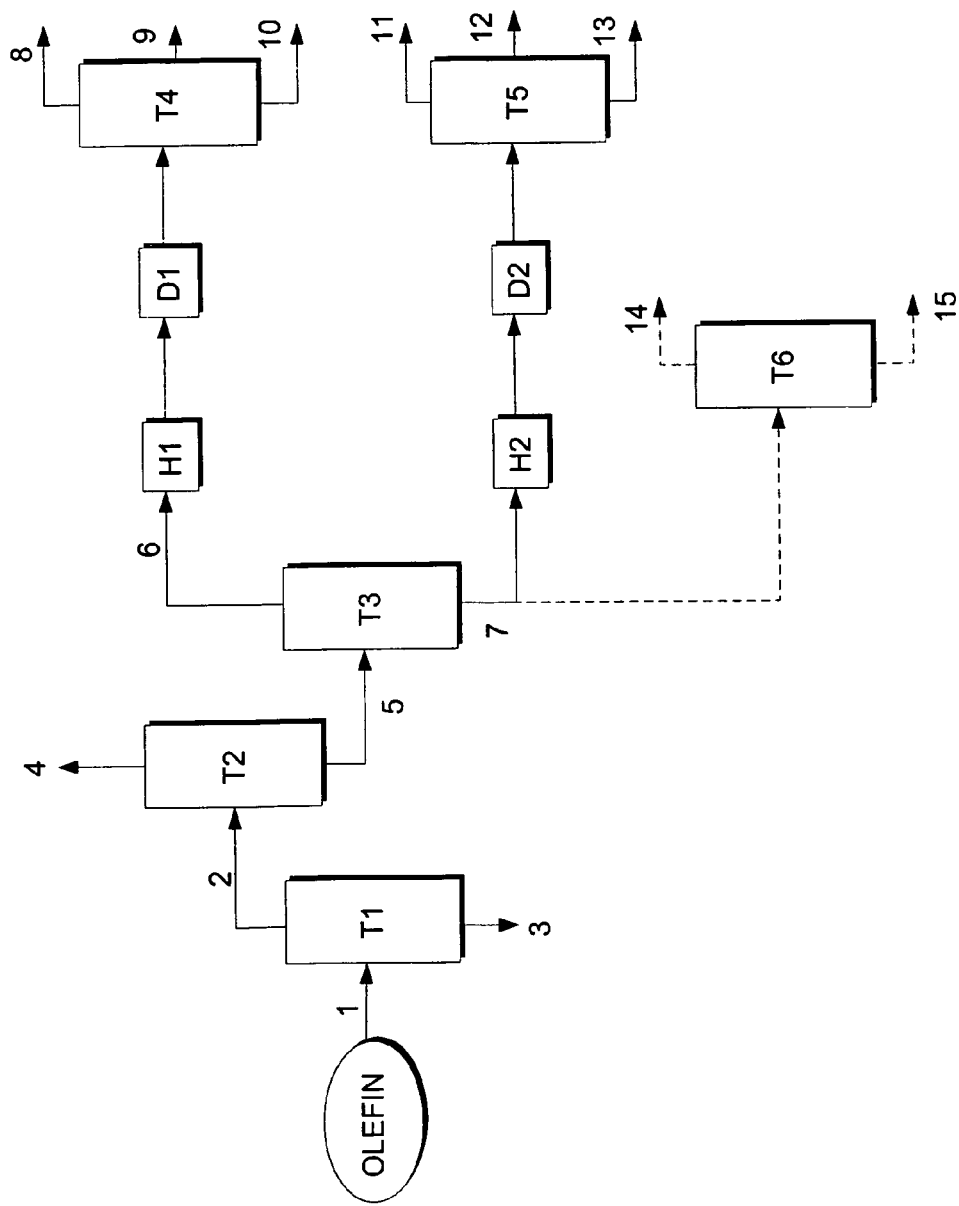
FIG. 2 is a flow diagram showing various propylene containing streams that can be used in the method of the present invention and also illustrates the concentration of a propylene containing stream obtained by the conversion of oxygenates to olefins to a high purity grade which is the preferred grade as a feed for hydroformylation. The concentration is effected by distillation, and rejection of most of the propane in the less pure product via the bottom of the superfractionation tower.

FIG. 2 shows an olefin stream (1) obtained by the conversion of oxygenates to olefins which is fed to a distillation column T1 where it is separated into a C2/C3 rich stream (2) and a C4 stream (3). The C2/C3 stream (2) is then fed to a second distillation tower T2 where hydrogen and carbon monoxide together with some ethylene are separated overhead as stream (4) and an ethylene/propylene stream is obtained as bottoms (5). This bottoms stream (5) is fed to a third distillation tower T3 where ethylene is separated overhead as stream (6) and a predominantly propylene stream is obtained as stream (7). The respective streams are then fed to hydrogenators H1 and H2 which are used to convert trace amounts of acetylenes and dienes to olefins and then to driers D1 and D2. Finally the streams may be fed to additional distillation towers T4 and T5, from which respective streams 8, 9, 10 and 11, 12, 13 may be separated. Optionally, (some of) stream (7) may be delivered to a distillation tower T6 from which streams 14, 15 may be separated. Table 1 sets out typical stream compositions and the present invention therefore allows flexibility in the feed composition according to the desired product of hydroformylation. For example, the invention envisages the use of any of streams 2, 5, 7, 10, 11, 12, 13, 14 and 15 as the feed for hydroformylation, and also any possible combinations thereof. If desired, also stream 4 may be added to the hydroformylation, bringing its contained hydrogen, CO and ethylene as potentially useful reagents to the reaction. FIG. 2 is further described hereinafter.

In a preferred embodiment the propylene containing fraction will be separated from the olefin product of the oxygenate to olefins reaction so as to contain at least 97 mole % of propylene, more preferably at least 97.5 mole %, most preferably at least 98 mole %, at least 99 mole %, at least 99.5 mole % or even at least 99.9 mole % of propylene. This type of separation will tend to leave a significant amount of dimethyl ether, which is likely present in the olefin product of the oxygenate to olefin process, in the propylene/propane containing fraction. Unexpectedly we have found that when the separated propylene containing stream containing at least 97 mole % propylene is used as a feed to a hydroformylation process which uses a rhodium catalyst, particularly a low pressure rhodium process, the dimethyl ether will not significantly affect the catalytic activity of the catalyst. Most of the balance in the propylene containing stream from the oxygenate to olefins reaction is typically propane. Without propane separation, or with only partial propane separation, the propane content of this stream is less than 3% mole, preferably at most 2.5% mole, more preferably at most 2% mole or 1.5% mole, even more preferably at most 1% mole and most preferably at most 0.5% mole. When propane is separated out, also a portion of the dimethyl ether may be separated out with it.

Processes for the production of propylene streams from oxygenates and the purification of such streams are described in U.S. Pat. Nos. 5,914,433, 5,960,643, 6,049,017 and WO 01/25174. Conventional processes can be used for removing undesirable components from the olefin feed stream of this invention. Such methods include water washing, caustic scrubbing, distillation, and fixed bed adsorption. Other desirable methods, such as those found in Kirk-Othmer Encyclopedia of Chemical Technology, 4th edition, Volume 9, John Wiley & Sons, 1996, pg. 894-899, the description of which is incorporated herein by reference, can also be used. In addition, purification systems such as that found in Kirk-Othmer Encyclopedia of Chemical Technology, 4th edition, Volume 20, John Wiley & Sons, 1996, pg. 249-271, the description of which is also incorporated herein by reference, can be used.

The sulphur content of the propylene feed used in the method of this invention, particularly as mercaptans but especially as carbonyl sulphide, is desirably sufficiently low that the activity of the catalyst used to form the hydroformylated product is not substantially inhibited. Ideally, the sulphur content in the propylene feed is not greater than about 1 ppm by weight on an atomic basis; progressively more preferably not greater than about 500 ppb, not greater than about 100 ppb, not greater than about 50 ppb, not greater than about 20 ppb, not greater than about 10 ppb, not greater than about 5 ppb, and most preferably, not greater than about 2 ppb by weight, calculated on an atomic basis.

The reactive nitrogen content of the propylene feed used in the method of this invention, excluding N2 but including reactive species like ammonia and amines, and particularly such highly reactive species as nitriles or other cyano compounds, are also desirably sufficiently low that the catalytic activity of the catalyst used to form the hydroformylated product is not substantially inhibited. Preferably, the active nitrogen content in the propylene feed is not greater than about 10 ppm; more preferably, not greater than about 5 ppm; and most preferably, not greater than about 2 ppm by weight, calculated on an atomic basis. More preferably, the active nitrogen content of the stream is not greater than about 1 ppm by weight on an atomic basis; progressively more preferably not greater than about 500 ppb, not greater than about 100 ppb, not greater than about 50 ppb, not greater than about 20 ppb, not greater than about 10 ppb, not greater than about 5 ppb, and most preferably, not greater than about 2 ppb by weight, calculated on an atomic basis. Ammonia itself may not have such a large effect on the catalytic activity of the catalyst, and may be tolerated in significantly higher amounts than nitrites or cyano compounds.

The chlorine content of the propylene feed used in this invention, in particular the ionic chlorine, is also desirably sufficiently low that the catalytic activity of the catalyst used to form the hydroformylated product is not substantially inhibited. Preferably, the chlorine content in the olefin feed is not greater than about 5 ppm; more preferably, not greater than about 2 ppm; and most preferably, not greater than about 1 ppm by weight, calculated on an atomic basis. More preferably, the ionic chlorine content of the stream is not greater than about 1 ppm by weight on an atomic basis; progressively more preferably not greater than about 500 ppb, not greater than about 100 ppb, not greater than about 50 ppb, not greater than about 20 ppb, not greater than about 10 ppb, not greater than about 5 ppb, and most preferably, not greater than about 2 ppb by weight, calculated on an atomic basis. Alkyl chlorides may not have such a large effect on the catalytic activity of the catalyst, and may be tolerated in significantly higher amounts than ionic chlorine.

We have found that the propylene containing stream contacted with the rhodium hydroformulation catalyst in the method of the invention may contain a non-toxic amount of dimethyl ether. This means that dimethyl ether may be present in the stream, which provides the advantage that treatment or removal is not necessary. However, excessive quantities are not desirable from the practical standpoint that in such cases the reactor volume is inefficiently utilized. A propylene stream containing up to about 5000 ppm by weight is highly acceptable. The lower the quantity of dimethyl ether, the greater the desirability from a hydroformylation operation standpoint. Feeds containing dimethyl ether at levels of up to about 4000 ppm by weight, up to about 3000 ppm by weight, up to about 2000 ppm by weight, up to about 1000 ppm by weight, up to about 500 ppm by weight, up to about 250 ppm by weight, may be used according to the invention.

Typical oxygenates that can be converted to olefins are methanol and its derivatives, but also other alcohols may be used. Particularly promising oxygenate candidates are alcohols, such as methanol and ethanol, dimethyl ether, methyl ethyl ether, diethyl ether, dimethyl carbonate, methyl formate, and mixtures thereof. The oxygenate or mixture of oxygenates can also be mixed with other fuel components, such as hydrocarbons or inerts. The catalyst composition used to convert the oxygenates to olefins preferably comprises from about 1% to about 99%, more preferably from about 5% to about 90%, and most preferably from about 10% to about 80%, by weight of molecular sieve. It is also preferred that the catalyst composition have a particle size of from about 20 µm to about 3,000 µm, more preferably from about 30 µm to about 200 µm, most preferably from about 50 µm to about 150 µm.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

A preferred catalyst contains a combination of SAPO-34, and SAPO-18 or ALPO-18 molecular sieve. In a particularly preferred embodiment, the molecular sieve is a crystalline intergrowth of SAPO-34, and SAPO-18 or ALPO-18.

Any standard reactor system can be used in the oxygenate to olefin process, including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 hr−1, preferably from about 1 hr−1 to about 1000 hr−1, more preferably from about 20 hr−1 to about 1000 hr−1, and most preferably from about 20 hr−1 to about 500 hr−1. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternatively, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

The pressure in the oxygenate to olefin process also may vary over a wide range, including autogenous pressures. Effective pressures may be, but are not necessarily limited to, oxygenate partial pressures of at least about 6 kpaa, preferably at least about 35 kpaa. The process is particularly effective at higher oxygenate partial pressures, such as an oxygenate partial pressure of greater than about 140 kpaa. Preferably, the oxygenate partial pressure is at least about 170 kpaa, more preferably at least about 2 MPaa. For practical design purposes it is desirable to operate at an oxygenate, eg methanol, partial pressure of not greater than about 3.5 MPaa, preferably not greater than about 2.8 MPaa, most preferably not greater than about 2.0 MPaa.

One way of increasing the olefin yield in the oxygenate to olefin process is to operate the process such that there is not 100% conversion of oxygenate to olefin product. This means that not all of the oxygenate feed will be completely converted to olefin or some other final product. Less than 100% conversion can mean that some of the oxygenate feed is not converted or that not all intermediate products are completely converted to olefin. For example, dimethyl ether can be used as a feed or it may form as an intermediate product in the conversion to olefin. Therefore, the presence of dimethyl ether in the olefin product will generally infer that the conversion of oxygenate to olefin is less than 100%.

In the method of this invention, it is desirable to separate a propylene rich stream from the olefin product stream produced in the oxygenate to olefin process. Dimethyl ether present in the olefin product stream will tend to separate with the propylene/propane rich stream. The advantage is that the propylene rich stream can be used as feed for a rhodium hydroformylation process to produce a hydroformylated product, i.e., normal or isobutyraldehyde, or normal or isobutanol, or a mixture of any of these. In this type of process, the presence of dimethyl ether will have little if any adverse impact on the catalytic activity of the rhodium catalyst. Another advantage in this type of separation is that a very pure ethylene stream can be obtained. Such a stream can then be used as feed to a polymerization unit with little to no additional pretreatment for removal of dimethyl ether, which is considered to be a poison to many polymerization catalysts.

Separation can be accomplished using conventional means, including distillation, rectification, fractionation, superfractionation and the like, which are all known and part of the state of the art and are illustrated schematically in FIG. 2.

Referring again to FIG. 2, after drying, the dried propylene stream (7) can also be further processed by sending to a distillation column T5. In T5 a propylene containing stream 11 also containing a substantial amount of ethylene is separated, as well as a propane rich stream 13. The recovered propylene rich stream 12 is highly pure and has a variety of end uses. It can also be used in a hydroformylation reaction system to produce a highly pure butanal product.

In an alternative embodiment, the propylene rich stream 7 can be sent to a distillation column T6. Particularly if stream 7 contains little or no C2 or other components that are lighter than propylene, a column T6 may be used to produce a concentrated propylene stream (14) overhead, and a bottom stream (15) containing most of the propane, methylacetylene and propadiene, which all are heavier boilers than propylene and can be separated from propylene by distillation. Such a bottom stream (15) would also contain a major proportion of the dimethylether present in stream 7. This embodiment does not require a selective hydrogenation step H2, nor its associated drying step D2. It is preferred if the disposition of stream 15 is as a fuel.

Typical stream compositions for the flow scheme without T6 are shown in Table 1.

TABLE 1

| | Stream Number | | | | | | | | | | | | |
|---|---|---|---|---|---|---|---|---|---|---|---|---|---|
| Comp. | 1 (wt %) | 2 (wt %) | 3 (wt %) | 4 (wt %) | 5 (wt %) | 6 (wt %) | 7 (wt %) | 8 (wt %) | 9 (wt %) | 10 (wt %) | 11 (wt %) | 12 (wt %) | 13 (wt %) |
| $H_2$ | 0.10 | 0 | 0 | 4 | 0 | 0 | 0 | 0 | 0 | 0 | 0 | 0 | 0 |
| CO | 0.05 | 0 | 0 | 2 | 0 | 0 | 0 | 0 | 0 | 0 | 0 | 0 | 0 |
| $CH_4$ | 1.55 | 2 | 0 | 61 | 0 | 0 | 0 | 24 | 0 | 0 | 0 | 0 | 0 |
| $C_2H_4$ | 40.35 | 48 | 0 | 32 | 48 | 95 | 2 | 76 | 100 | 13 | 33 | 0 | 0 |
| $C_2H_6$ | 1.24 | 1 | 0 | 1 | 1 | 3 | 0 | 0 | 0 | 52 | 1 | 0 | 0 |
| $C_3H_6$ | 40.35 | 47 | 5 | 0 | 48 | 2 | 94 | 0 | 0 | 34 | 66 | 100 | 21 |
| $C_3H_8$ | 1.24 | 1 | 0 | 0 | 1 | 0 | 3 | 0 | 0 | 1 | 0 | 0 | 63 |
| $C_4^+$ | 15.11 | 0 | 95 | 0 | 0 | 0 | 1 | 0 | 0 | 0 | 0 | 0 | 16 |
| (total) | 100.00 | 100 | 100 | 100 | 100 | 100 | 100 | 100 | 100 | 100 | 100 | 100 | 100 |

Note:
Oxygenates, trace hydrocarbon components such as e.g. acetylenes, dienes and CO2 are not accounted for in this material balance, although they may be present.

The preferred propylene containing feed stream of this invention should contain at least 96 wt % propylene. More concentrated streams are still more desirable. For example, propylene streams containing at least about 96.5 wt %, 97 wt %, 97.5 wt %, 98% wt, 98.5% wt, 99% wt, 99.5% wt, 99.7% wt and 99.9 wt % are progressively more desirable.

It is also desirable that the propylene containing feed stream be separated so as to contain a lesser amount of ethylene. A preferred propylene containing feed stream contains less than about 1 wt % ethylene. Streams may contain even lesser amounts of ethylene are preferred. For example, propylene streams containing not greater than about 5000 ppm wt ethylene, not greater than about 2500 ppm wt ethylene, not greater than about 2000 ppm wt ethylene, not greater than about 1000 ppm wt ethylene, not greater than about 500 ppm wt ethylene, not greater than about 100 ppm wt ethylene, not greater than about 50 ppm wt ethylene, not greater than about 30 ppm wt ethylene, not greater than about 20 ppm wt ethylene, and not greater than about 10 ppm wt ethylene are more progressively preferred.

In one embodiment it is desirable in this invention to limit the amount of C4 unsaturates, i.e. butenes, butadiene and other C4 polyunsaturates, in the propylene containing stream. The propylene containing feed stream preferably contains less than about 1% wt of C4 unsaturates. Streams containing even lesser amounts of C4 unsaturates are preferred. For example, propylene streams containing not greater than 5000 ppm wt of C4 unsaturates, not greater than 1000 ppm wt of C4 unsaturates, not greater than 500 ppm wt of C4 unsaturates, not greater than 100 ppm wt of C4 unsaturates, not greater than 50 ppm wt of C4 unsaturates, not greater than 10 ppm wt of C4 unsaturates, and not greater than 7 ppm wt C4 unsaturates are more progressively preferred.

An olefin product obtained by reacting oxygenates with molecular sieve catalysts requires little if any treatment to remove certain other contaminants. For example, little if any treatment is needed to remove compounds containing sulfur, nitrogen and chlorine which act as poisons to various polymer and hydroformylation catalysts.

The hydroformylation reaction can be carried out using conventional hydroformylation catalysts or catalyst precursors. Such reaction involves contacting olefin, carbon monoxide and hydrogen in the presence of a hydroformylation catalyst or precursor.

Rhodium hydroformylation catalysts are particularly desirable in this invention, because they are particularly tolerant to the presence of dimethyl ether. Suitable rhodium catalysts or catalyst precursors which can be used in this invention include rhodium(II) and rhodium(III) salts such as rhodium(III) chloride, rhodium(III) nitrate, rhodium(III) sulfate, potassium rhodium sulfate (rhodium alum), rhodium(II) or rhodium(III) carboxylate, preferably rhodium(II) and rhodium(III) acetate, rhodium(III) oxide, salts of rhodic(III) acid, triammonium hexachlororhodate (III).

In one embodiment of the invention, hydroformylation is carried out using an oil-soluble rhodium complex comprising a low valence rhodium (Rh) complexed both with carbon monoxide and a triorganophosphorus compound. The triorganophosphorus compound can include one or more oil-soluble triarylphosphines, trialkylphosphines, alkyl-diarylphosphines, aryl-dialkylphosphines, triorganophosphites, particularly trialkylphosphites and triarylphosphites (in which list alkyl includes cycloalkyl), containing one or more phosphorus atoms per molecule capable of complexing with Rh by virtue of having a lone pair of electrons on the phosphorus.

In another embodiment, triorganophosphorus ligands can be used which preferably have (a) a molar P:Rh ratio of at least about 2:1, (b) a total concentration of phosphorus of at least about 0.01 mol/l; and (c) a [P]/Pco ratio maintained in the reactor of at least about 0.1 mmol/l/kPa, where [P] is the total concentration of the phosphorus in solution expressed in mmol per liter, and Pco is the partial pressure of carbon monoxide in the gas phase.

Examples of triorganophosphorus ligands include trioctylphosphine, tricyclohexylphosphine, octyldiphenylphosphine, cyclohexyldiphenylphosphine, phenyldioctylphosphine, phenyldicyclohexylphosphine, triphenylphosphine, tri-p-tolylphosphine, trinaphthylphosphine, phenyl-dinaphthylphosphine, diphenylnaphthylphosphine, tri-(p-methoxyphenyl)phosphine, tri-(p-cyanophenyl)phosphine, tri-(p-nitrophenyl)phosphine, and p-N,N-dimethylaminophenyl(diphenyl)phosphine, trioctylphosphite or tri-p-tolylphosphite. An example of a bidentate compound which can be used is diphos-bis(diphenylphosphino)ethane.

Preferably, Rh concentration in the reaction mixture is in a range of from about 1×10−5 to about 1×10−2 moles/liter or, in effect, in a range of from about 1 to about 1000 ppm or about 10 to 1000 ppm, preferably about 20 to about 500 ppm, more preferably from 25 to 350 ppm of rhodium, based on the total weight of the solution present in the hydroformylation reactor employed in the method.

Organophosphite ligands can also be used for example those disclosed in U.S. Pat. Nos. 4,599,206, 4,668,651, 4,737,588, 4,748,261, 4,769,498, 4,774,361, 4,789,753, 4,835,299, 4,871,880, 4,885,401, 5,179,055, 5,288,918, 5,312,996, 5,364,950, 5,681,473, 5,756,855 and WO 97/20793. Preferred is 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin, or 6,6'-[[3,3',5,5'-tetrakis(1,1-dimethylpropyl)-1,1'-biphenyl-2,2'-diyl]bis(oxy)]bis-dibenzo[d,f][1,3,2]-dioxaphosphepin, or 6,6'-[[3,3'-bis(1,1-dimethylethyl)-5,5'-dimethoxy[1,1'-biphenyl]-2,2'-diyl]bis(oxy)]bis-dibenzo[d,f][1,3,2]-dioxaphosphepin, or tris(2,4,6-di-t-butylphenyl)-phosphite. Most preferred is 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin. Ionic varieties of such phosphites are disclosed in U.S. Pat. Nos. 5,059,710 and 5,113,022.

More recently bisphosphite ligands, e.g. of the formula

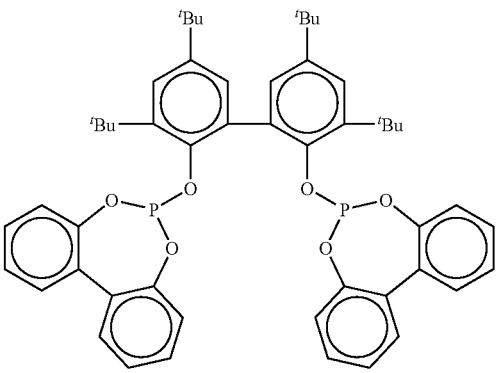

have been developed and these are described in U.S. Pat. Nos. 5,364,950, 4,835,299 and 5,288,918.

The present invention relates to improvements in or relating to the commercial scale (eg at least 3 tonnes per hour) hydroformylation of propylene to produce butyraldehyde and butanol.

The hydroformylation of propylene to produce butyraldehyde and butanol is well known and is practised widely, typically employing liganded rhodium catalysed low pressure hydroformylation technology, sometimes known as the low pressure oxo (LPO) process, in which propylene is reacted with a mixture of carbon monoxide and hydrogen (known as syngas). Examples of the commercial operation of such a process are given in U.S. Pat. No. 4,247,486 and in GB patent 1,387,657.

For economic reasons on an industrial scale the raw material for such a process has been chemical grade propylene which contains about 90-95 wt % propylene with the majority of the balance being propane. The industrial hydroformylation processes are generally continuous processes which do not result in 100% conversation of the propylene. The selectivity to desired products is also not 100%, and a small portion of the propylene is hydrogenated to propane. Accordingly the products of the hydroformylation of chemical grade propylene include the butyraldehyde and butanol stream and an off gas stream containing unreacted propylene, propane and unreacted carbon monoxide and hydrogen.

It is of course economically desirable that the unreacted propylene, carbon monoxide and hydrogen be recycled. However, in order for the continuous hydroformylation process to operate successfully on an industrial scale, it is important to establish a steady state between the feed materials, including any recycle, and the degree of reaction. It is therefore important to prevent excessive propane build up in the reaction system due to the recycle of the unreacted components. However, propane and propylene are difficult to separate and thus, in order to prevent propane build up due to the recycle, it is necessary to vent off some if not all of the propane. This removal of propane however also involves the removal of some propylene resulting in some inefficiencies and economic debits in the process.

The catalyst is desirably contacted with the propylene feed stream in solution. The solution can comprise an oily solvent or a mixture of such solvents. For example, aliphatic and aromatic hydrocarbons (e.g., heptanes, cyclohexane, toluene), esters (e.g., dioctyl phthalate), ethers, and polyethers (e.g., tetrahydrofuran, and tetraglyme), aldehydes (e.g., propanal, butanal) the condensation products of the oxo product aldehydes or the triorganophosphorus ligand itself (e.g., triphenylphosphine).

Alternatively, as described in U.S. Pat. Nos. 4,248,802, 4,808,756, 5,312,951 and 5,347,045, which are each incorporated herein by reference, the catalyst may contain a hydrophilic group. In such a case, an aqueous medium may be used.

Rhodium can be introduced into the reactor as a preformed catalyst, for example, a solution of hydridocarbonyl tris(triphenylphosphine)rhodium(I); or it can be formed in situ. If the catalyst is formed in situ, the Rh may be introduced as a precursor such as acetylacetonatodicarbonyl rhodium(I) {Rh(CO)2(acac)}, rhodium oxide {Rh2O3}, rhodium carbonyls {Rh4(CO)12, Rh6(CO)16}, tris(acetylacetonato)rhodium(I), {Rh(acac)3}, or a triaryl phosphine-substituted rhodium carbonyl {Rh(CO)2(PAr3)}2, wherein Ar is an aryl group.

Hydroformylation is desirably carried out at a temperature of from about 40 to about 200° C., more desirably from about 80 to about 180° C., and preferably from about 90 to about 155° C.

The reaction is also desirably carried out at a low pressure, e.g., a pressure of about 0.05 to about 10 MPa (absolute), preferably about 0.1 to about 8 MPaa, and most preferably below about 5 MPaa. It is particularly preferred that carbon monoxide partial pressure be not greater than about 50% of the total pressure. The proportions of carbon monoxide and hydrogen used in the hydroformylation or oxo reactor at the foregoing pressures are desirably maintained as follows: CO from about 1 to about 50 mol %, preferably about 1 to about 35 mol %; and H2 from about 1 to about 98 mol %, preferably about 10 to about 90 mol %.

The hydroformylation reaction can be conducted in a batch mode or, preferably, on a continuous basis. In a continuous mode, a residence time as short as 10 or 20 seconds, or of up to 4 hours can be used. If a plurality of reactors is employed, a residence time as short as 10 to 15 seconds can be employed. Otherwise a preferred residence time is in the range of from about 30 seconds to about 5 minutes.

Since the hydroformylation stage of the invention advantageously takes place in the liquid phase and the reactants are gaseous compounds, a high contact surface area between the gas and liquid phases is desirable to avoid mass transfer limitations. A high contact surface area between the catalyst solution and the gas phase can be obtained in a variety of ways, for example, by stirring in a batch autoclave operation. In a continuous operation, the olefin feed stream can be contacted with catalyst solution in, for example, a continuous-flow stirred autoclave where the feed is introduced and dispersed at the bottom of the vessel, preferably through a perforated inlet. Good contact between the catalyst and the gas feed can also be ensured by dispersing a solution of the catalyst on a high surface area support. Such a technique is commonly referred to as supported liquid phase catalysis. The catalyst can also be provided as part of a permeable gel.

The hydroformylation reaction can be performed in a single reactor. Examples of suitable reactors can be found in U.S. Pat. Nos. 4,287,369 and 4,287,370; U.S. Pat. No. 4,322,564; U.S. Pat. No. 4,479,012 and EP-A-114,611; EP-A-103,810 and EP-A-144,745. Two or more reactor vessels or reactor schemes configured in parallel can also be used. In addition, a plug flow reactor design, optionally with partial liquid product backmixing, can give an efficient use of reactor volume.

It is preferred that the hydroformylation reaction be carried out in more than one reaction zone or vessel in series. Suitable reactor configurations are disclosed, for example, in British Patent Specification No. 1,387,657, in U.S. Pat. No. 4,593,127, in U.S. Pat. No. 5,105,018, and in U.S. Pat. No. 5,367,106. Examples of individual hydroformylation reactors can be of the standard types described by Denbigh and Turner in "Chemical Reactor Theory" ISBN 0 521 07971 3, by Perry et al in "Chemical Engineers' Handbook" ISBN 0-07-085547-1 or any more recent editions, e.g., a continuous stirred tank or a plug flow reactor with adequate contact of the gas and the liquid flowing through the reactor. Advantageously these plug flow reactor designs or configurations include ways of partial backmixing of the reactor product liquid, as explained, for example, in EP-A-3,985 and in DE 3,220,858.

Where high purity propylene is used as the feed, the products will be predominantly butyraldehydes and may be a mixture of normal and isobutyraldehyde. Where the feed also contains ethylene the product will be a mixture of butyraldehydes and propionaldehyde.

The aldehydes produced in the present invention have utility as intermediates in the manufacture of numerous commercially important chemicals, with the invention further providing processes in which hydroformylation is followed by reactions producing such chemicals. The aldehyde products of this invention will have especial value when the aldehydes are aldolized, reacted with formaldehyde to produce polyols, hydrogenated to saturated alcohols, and the alcohols or acids esterified, etherified or formed into acetals to give plasticizers or synthetic lubricants. Under circumstances where the olefin feed is ultimately derived from a low-value feedstock like natural gas, i.e., in cases where methane from natural gas is converted to methanol and the methanol to olefin, the products or product mixtures from aldolization and hydrogenation may have value as liquid transportable fuels, optionally after dehydration to the olefin, and if desired hydrogenation to a paraffin or paraffinic mixture.

More especially, the invention provides a method for the manufacture of normal butanol and/or isobutanol, wherein any of the aldehydes formed by hydroformylation is hydrogenated. In addition, the invention provides a method for the manufacture of n-butyric and/or isobutyric acid, wherein any of the aldehyde product is oxidized; a method for the manufacture of an aldol dimer or trimer, wherein the aldehyde product is self-aldolized; in particular, n-butyraldehyde is aldolized and hydrogenated to produce 2-ethyl hexanol, a method for the manufacture of a saturated aldehyde, wherein the aldol dimer or trimer is hydrogenated to a corresponding saturated aldehyde; a method for the manufacture of an unsaturated alcohol, wherein the aldol dimer or trimer is selectively hydrogenated; a method for the manufacture of a saturated alcohol, wherein all double bonds in the aldol dimer or trimer are fully hydrogenated; a method for the manufacture of a saturated alcohol or acid, wherein the saturated aldehyde produced by hydrogenation of the aldol dimer or trimer is hydrogenated or oxidized to form the corresponding saturated alcohol or acid; a process for the manufacture of an ester, wherein the saturated alcohol or the acid is esterified, the ester possibly being a phthalate, adipate trimellitate or a polyol ester; a process for the manufacture of an aldol tetramer or pentamer, or mixtures thereof, by aldolization of the aldehyde mixture from hydroformylation; a process for the manufacture of a C6 to C20 alcohol or alcohol mixture, wherein the aldol dimer, trimer, tetramer, pentamer, or mixture, is hydrogenated to the corresponding alcohol or alcohol mixture; a process for the manufacture of liquid olefin or olefin mixture, wherein the tetramer or pentamer alcohol is dehydrated; and a process for the manufacture of a liquid paraffin or paraffin mixtures, wherein the olefin mixture is hydrogenated.

EXAMPLE 1

The example illustrates the production of butyraldehyde by the hydroformylation of chemical grade propylene and propylene (containing 97.5 mole % propylene) such as that which can be obtained from oxygenates The production from Chemical Grade Propylene is included for comparison.

The material balances are derived for a hydroformylation conducted by the process illustrated in FIG. 1 which shows a simplified flow scheme of a butyraldehyde process using low pressure rhodium hydroformylation technology. Propylene feed (1) and syngas feed (2) are mixed with gas recycle stream (5) and fed to the hydroformylation (LPO) reactor (100). Leaving the overhead entrainment separator (101) is reactor effluent (4), which after cooling in condenser (102) is separated into gas and liquid in separator (103). The gas from this separator is partially purged as vent gas (6), and the remainder is recycled via first compressor (104). The liquid from separator (103) is fed to a stabiliser (105), although some may be returned via line 10 to the LPO reactor (100). In stabiliser (105), light components are removed as stabiliser overhead gas (9), which is recycled by second compressor (106) to the gas recycle loop that is driven by the first compressor (104). Most of the butyraldehyde product leaves with the stabiliser bottom stream (8). Although the invention is also advantageous in other possible low pressure rhodium hydroformylation flow schemes known in the art, it is particularly advantageous for the process illustrated in FIG. 1.

Calculated Plant Material Balance

| Propylene feed quality | | Chemical Grade (CG) | Oxygenates to olefins | Relative to CG |
|---|---|---|---|---|
| Propylene content | Mole % | 95.0 | 97.5 | 95.0% |
| Propylene feed (1) flow | kg/h | 10000 | 9971 | 99.7% |
| Contained propylene | kg/h | 9477 | 9710 | 102.5% |
| Syngas feed (2) flow | kg/h | 6460 | 6662 | 103.1% |
| Propylene converted | kg/h | 8841 | 9127 | 103.2% |
| Butyraldehyde (n + iso) production rate | | | | |
| As recovered [in (8)] | kg/h | 14634 | 15106 | 103.2% |
| Vent gas by-product (6) flow | kg/h | 1751 | 1449 | 82.8% |
| Product utilization (flows per unit of butyraldehyde recovered) | | | | |
| Propylene feed (1) | kg/kg | 0.683 | 0.689 | 95.6% |
| Syngas feed (2) | kg/kg | 0.491 | 0.441 | 99.90% |
| Total feeds (1 + 2) | kg/kg | 1.125 | 1.101 | 97.9% |
| Vent gas by-product (6) | kg/kg | 0.120 | 0.096 | 81.02% |

EXAMPLE 2

This example illustrates the hydroformylation of propylene obtainable from oxygenates and the impact of various impurities therein.

It was found that methyl mercaptan when present in propylene, impairs rhodium catalysed hydroformylation. Beside the reaction rate reduction, it was found that such sulphur components react in the process with formation of higher boiling sulphur species.

Surprisingly it was found that dimethyl ether has marginal or no effect on the reaction rate and these components were found unchanged in the product after reaction.

More particularly, it was found that:

Methyl mercaptan, when present in a S/Rh molar ratio of 20/1, decreased the hydroformylation rate of propylene in a low pressure Rh/triphenyl phospine (TPP) hydroformylation kinetic experiment by 90% compared to a reference experiment without methyl mercaptan.

Dimethyl ether (DME), when present in a DME/Rh molar ratio of 20/1 and 80/1 showed no effect on the hydroformylation rate of propylene compared to the reference experiments without DME.

This therefore illustrates the benefits derived from the use of feeds low in sulphur such as those obtained by the conversion of oxygenates to olefins.

Hydroformylation kinetic experiments were carried out in a standard half liter zipperclave from Autoclave Engineers. Mixing occurred with an air driven stirrer with speed controlled at 2000 revolutions per minute. The mixer had a six bladed impeller that guaranteed a strong mixing between the gas and the liquid phase. Baffles inside the reactor prevented vortex formation and created back mixing. The reaction temperature was controlled at 110° C.+/−1° C. Pressure was controlled at 1000 kpag±10 kPa (10 barg+/−0.1 bar). Synthesis gas (48% H2 and 52% CO) was delivered from a calibrated high pressure storage cylinder equipped with a pressure transmitter allowing pressure reading at 1 kPa (0.01 bar) accuracy.

Each experiment started with a catalyst solution of the following composition:
Triphenyl phosphine (TPP)=19.84 g
Tetraglyme (solvent)=191.2 g
Rhodium=0.00576 g The rhodium was dosed using rhodium carbonyl acetylacetonate as catalyst precursor.

The catalyst solution contained 27 wtppm rhodium.

The catalyst solution was transferred into the reactor and the reactor was purged several times with syngas to remove air. The reactor content was then heated up to 110° C. under 200 kpag (2 barg) syngas pressure. Once the desired reaction temperature was reached, about 0.05 mol propylene was injected into the catalyst solution by means of synthesis gas and at the same time as the injection of propylene the pressure was adjusted to 1000 kpag (10 barg).

Immediately after the substrate injection and pressure adjustment, the progress of the reaction was followed by measuring the rate of gas consumption, indicated by the pressure decay (DELTA-P) in the high pressure syngas storage cylinder.

The reaction was run for 3 hours and at the end of the reaction the gas supply was stopped and the reactor was cooled down to room temperature. A gas sample was taken from the gas phase inside the reactor and analysed on a HP6890 gas chromatograph (supplied by Hewlett-Packard). The chromatograph was equipped with a thermal conductivity detector (TCD) detection system and a poraplotQ column of 30 m length, 0.53 mm internal diameter (ID), 10 μm df (standing for "dense phase" and indicating film thickness). A liquid sample was withdrawn from the reactor into a cooled sample vial and analysed for product composition by gas chromatography using a HP6890 gaschromatograph equipped with a Flame Ionisation Detector (FID) detection system and a wall coated open tubular (WCOT) Ultimetal column of 10 m length, 0.53 mm ID, 0.17 μm df. The column (HTSimdistCB) is a chemically bound high temperature simulated distillation column. "Ultimetal" and "poraplotQ" are trade names of the Varian-Chrompack company. For the determination of dimethyl ether a second analysis was carried out over a Chrompack CP Wax 52 fused silica column of 50 m length, 0.25 mm ID, 0.2 μm df.

Sulfur analyses of the products were performed on a HP6890 gas chromatograph equipped with a fused silica column and a model 355 flameless sulphur chemoluminescence detector from Sievers. The column was a CPSIL5CB chemically bound silica column supplied by Chrompack of 30 m length, 0.32 mm ID and 5 μm df. This method gives quantitative information both about total sulfur and about individual sulphur components in the product with a detection limit of about 5 wtppb.

Finally the reactor was depressurised and the liquid recovered and weighed. From the weight of the product, its composition and the composition of the off-gas the end-conversion was calculated. The conversion at any given moment could then be calculated pro-rata the pressure drop at that moment, the measured end-conversion and the total pressure drop achieved at the end of the experiment.

Two experiments served as reference case, providing a base case reaction rate for propylene hydroformylation with rhodium and triphenyl phosphine in absence of any impurity. The two runs also served to demonstrate the reproducibility of the experiments and the results of these experiments are shown in Tables 2 and 3. In those Tables, TPP stands for triphenyl phosphine; TPPO stands for triphenyl phosphine oxide; and TEGDE stands for tetra-ethylene glycol dimethyl ether (also known as tetraglyme).

Figure 3:
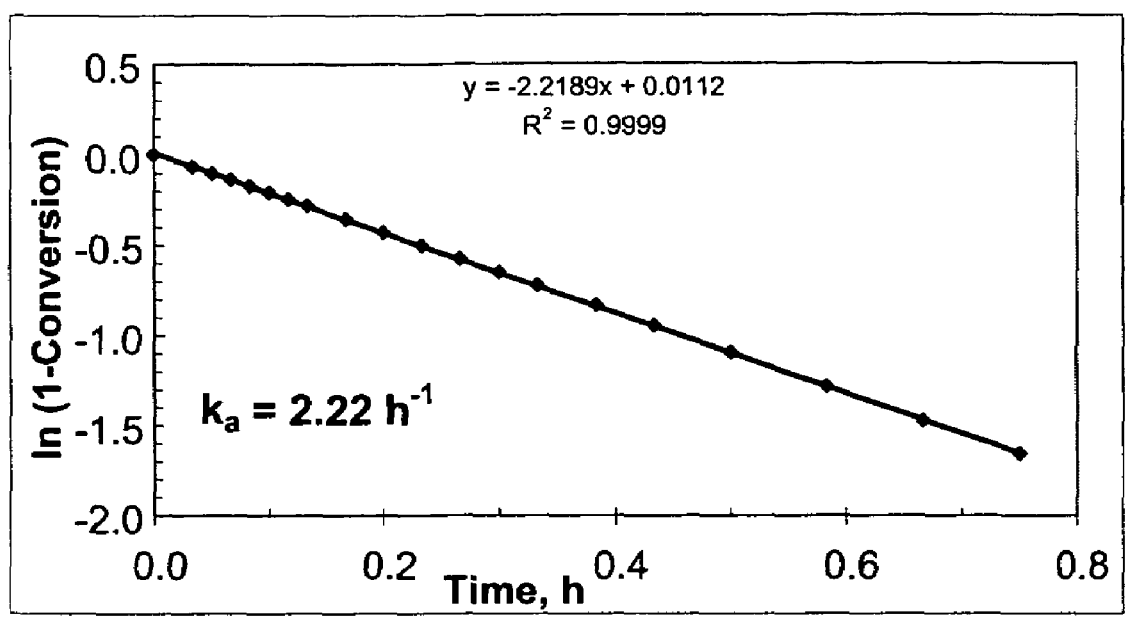
FIGS. 3-7 graph the conversion data found in Tables 2-6.
Figure 4:
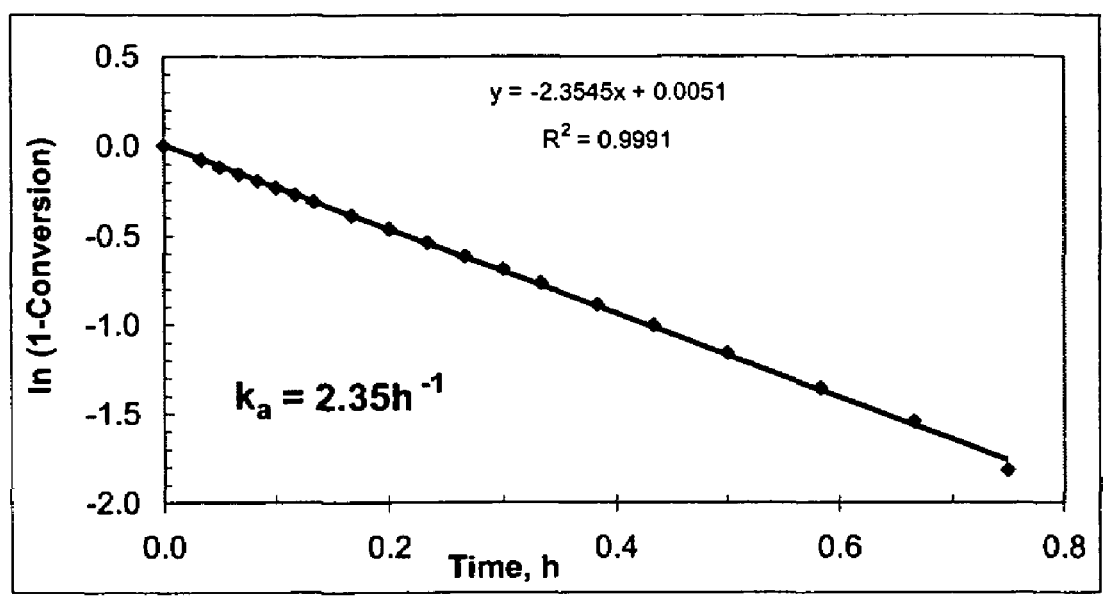

At 110° C. the graphs of ln(1-conversion) versus time in FIGS. 3 and 4 showed a linear slope, and first order reaction rates of 2.22 h−1 and 2.35 h−1 were measured respectively for the two reference runs.

TABLE 2

Propylene reference run 1

| PRODUCT COMPOSITION | Wt % | g | moles |
|---|---|---|---|
| Propylene | 0.01 | 0.02 | 0.0005 |
| i-butanal | 0.48 | 1.00 | 0.0139 |
| n-butanal | 1.85 | 3.86 | 0.0536 |
| TPP | 9.43 | 19.70 | 0.0751 |
| TPPO | 0.48 | 1.00 | 0.0036 |
| Butyric acid | 0.03 | 0.06 | 0.0007 |
| TEGDE | 87.71 | 183.23 | 0.8243 |
| C3 in off gas | | 0.0110 | 0.0003 |
| Substrate conversion | 98.80% molar | | |

| time, min | DELTA P | Conversion | 1-conversion | ln(1-conv) |
|---|---|---|---|---|
| 0 | 0.000 | 0.000 | 1.000 | 0.000 |
| 2 | 0.860 | 6.561 | 0.934 | −0.068 |
| 3 | 1.290 | 9.842 | 0.902 | −0.104 |
| 4 | 1.690 | 12.893 | 0.871 | −0.138 |
| 5 | 2.090 | 15.945 | 0.841 | −0.174 |
| 6 | 2.490 | 18.996 | 0.810 | −0.211 |
| 7 | 2.860 | 21.819 | 0.782 | −0.246 |
| 8 | 3.210 | 24.489 | 0.755 | −0.281 |
| 10 | 3.930 | 29.982 | 0.700 | −0.356 |
| 12 | 4.580 | 34.941 | 0.651 | −0.430 |
| 14 | 5.180 | 39.519 | 0.605 | −0.503 |
| 16 | 5.740 | 43.791 | 0.562 | −0.576 |
| 18 | 6.270 | 47.834 | 0.522 | −0.651 |
| 20 | 6.750 | 51.496 | 0.485 | −0.724 |
| 23 | 7.420 | 56.608 | 0.434 | −0.835 |
| 26 | 8.030 | 61.262 | 0.387 | −0.948 |
| 30 | 8.730 | 66.602 | 0.334 | −1.097 |
| 35 | 9.480 | 72.324 | 0.277 | −1.285 |
| 40 | 10.110 | 77.130 | 0.229 | −1.475 |
| 45 | 10.610 | 80.945 | 0.191 | −1.658 |
| 50 | 11.060 | 84.378 | 0.156 | −1.856 |
| 55 | 11.410 | 87.048 | 0.130 | −2.044 |
| 60 | 11.690 | 89.184 | 0.108 | −2.224 |
| 90 | 12.530 | 95.592 | 0.044 | −3.122 |
| 120 | 12.830 | 97.881 | 0.021 | −3.854 |
| 180 | 12.950 | 98.797 | 0.012 | −4.420 |

TABLE 3

Propylene reference run 2

| PRODUCT COMPOSITION | Wt % | g | moles |
|---|---|---|---|
| Propylene | 0.01 | 0.02 | 0.0005 |
| i-butanal | 0.43 | 0.90 | 0.0125 |
| n-butanal | 1.67 | 3.49 | 0.0484 |
| TPP | 9.27 | 19.39 | 0.0740 |
| TPPO | 0.55 | 1.15 | 0.0041 |
| Butyric add | 0.04 | 0.08 | 0.0009 |
| TEGDE | 88.03 | 184.16 | 0.8285 |
| C3 in off gas | | 0.0083 | 0.0002 |
| Substrate conversion | 98.61% molar | | |

| time, min | DELTA P | Conversion | 1-conversion | ln(1-conv) |
|---|---|---|---|---|
| 0 | 0.000 | 0.000 | 1.000 | 0.000 |
| 2 | 0.890 | 7.732 | 0.923 | −0.080 |
| 3 | 1.300 | 11.294 | 0.887 | −0.120 |
| 4 | 1.680 | 14.596 | 0.854 | −0.158 |
| 5 | 2.050 | 17.810 | 0.822 | −0.196 |
| 6 | 2.400 | 20.851 | 0.791 | −0.234 |
| 7 | 2.750 | 23.892 | 0.761 | −0.273 |
| 8 | 3.090 | 26.846 | 0.732 | −0.313 |

TABLE 3-continued

Propylene reference run 2

| | | | | |
|---|---|---|---|---|
| 10 | 3.700 | 32.146 | 0.679 | −0.388 |
| 12 | 4.280 | 37.185 | 0.628 | −0.465 |
| 14 | 4.800 | 41.702 | 0.583 | −0.540 |
| 16 | 5.300 | 46.046 | 0.540 | −0.617 |
| 18 | 5.750 | 49.956 | 0.500 | −0.692 |
| 20 | 6.170 | 53.605 | 0.464 | −0.768 |
| 23 | 6.770 | 58.818 | 0.412 | −0.887 |
| 26 | 7.290 | 63.335 | 0.367 | −1.003 |
| 30 | 7.900 | 68.635 | 0.314 | −1.159 |
| 35 | 8.550 | 74.282 | 0.257 | −1.358 |
| 40 | 9.050 | 78.626 | 0.214 | −1.543 |
| 45 | 9.640 | 83.752 | 0.162 | −1.817 |
| 50 | 9.850 | 85.577 | 0.144 | −1.936 |
| 55 | 10.070 | 87.488 | 0.125 | −2.078 |
| 60 | 10.300 | 89.486 | 0.105 | −2.252 |
| 90 | 11.100 | 96.437 | 0.036 | −3.334 |
| 120 | 11.300 | 98.174 | 0.018 | −4.003 |
| 180 | 11.350 | 98.609 | 0.014 | −4.275 |

In a third experiment, about 250 wtppm methyl mercaptan was added to the catalyst solution to provide a S/Rh molar ratio of 20. The first order reaction rate of propylene hydroformylation dropped to 0.27 $h^{-1}$ or a decrease of about 88-89%.

Methyl mercaptan is clearly a strong inhibitor in the hydroformylation of propylene with rhodium and triphenylphosphine at low pressure.

Figure 5:
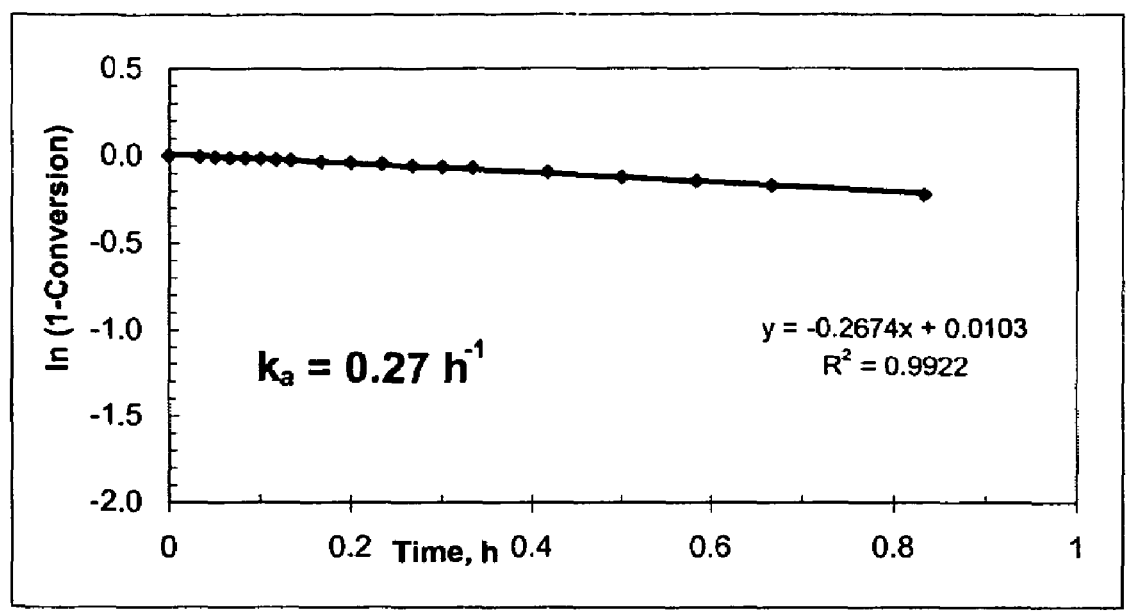

In the final product 195 wtppm of the total sulphur was detected as original methyl mercaptan, while the rest of the sulfur had been transformed into heavier sulphur species. The results are shown in Table 4 and FIG. 5.

TABLE 4

Effect of methylmercaptan

| PRODUCT COMPOSITION | Wt % | g | moles |
|---|---|---|---|
| Propylene | 0.35 | 0.73 | 0.0174 |
| i-butanal | 0.38 | 0.80 | 0.0110 |
| n-butanal | 1.52 | 3.18 | 0.0441 |
| TPP | 9.82 | 20.55 | 0.0784 |
| TPPO | 0.16 | 0.33 | 0.0012 |
| Butyric acid | 0.03 | 0.06 | 0.0007 |
| TEGDE | 87.72 | 183.60 | 0.8260 |
| C3 in off gas | | 0.1700 | 0.0040 |
| Substrate conversion | | 57.02% molar | |
| Sulfur in product, wtppm | | 238 | |

| time, min | DELTA P | Conversion | 1-conversion | ln(1-conv) |
|---|---|---|---|---|
| 0 | 0.000 | 0.000 | 1.000 | 0.000 |
| 2 | 0.090 | 0.524 | 0.995 | −0.005 |
| 3 | 0.120 | 0.699 | 0.993 | −0.007 |
| 4 | 0.170 | 0.990 | 0.990 | −0.010 |
| 5 | 0.220 | 1.281 | 0.987 | −0.013 |
| 6 | 0.270 | 1.573 | 0.984 | −0.016 |
| 7 | 0.370 | 2.155 | 0.978 | −0.022 |
| 8 | 0.430 | 2.505 | 0.975 | −0.025 |
| 10 | 0.550 | 3.203 | 0.968 | −0.033 |
| 12 | 0.670 | 3.902 | 0.961 | −0.040 |
| 14 | 0.780 | 4.543 | 0.955 | −0.046 |
| 16 | 0.940 | 5.475 | 0.945 | −0.056 |
| 18 | 1.060 | 6.174 | 0.938 | −0.064 |
| 20 | 1.130 | 6.582 | 0.934 | −0.068 |
| 25 | 1.580 | 9.203 | 0.908 | −0.097 |
| 30 | 1.970 | 11.474 | 0.885 | −0.122 |
| 35 | 2.320 | 13.513 | 0.865 | −0.145 |
| 40 | 2.680 | 15.610 | 0.844 | −0.170 |
| 50 | 3.450 | 20.094 | 0.799 | −0.224 |
| 60 | 3.810 | 22.191 | 0.778 | −0.251 |
| 90 | 5.240 | 30.520 | 0.695 | −0.364 |

TABLE 4-continued

Effect of methylmercaptan

| | | | | |
|---|---|---|---|---|
| 120 | 6.840 | 39.839 | 0.602 | −0.508 |
| 180 | 9.790 | 57.021 | 0.430 | −0.844 |

In two further experiments, either 0.024 wt % or 0.1 wt % of dimethylether (DME) were injected in the catalyst solution, corresponding to molar ratios of DME/Rh of 20 and 82 respectively.

First order reaction rates of 2.21 h−1 and 2.28 h−1 were measured, showing no significant change from the reference runs where no DME was present.

It may be concluded that DME has no significant inhibiting effect on the hydroformylation rate of propylene in a low pressure rhodium system.

Figure 6:
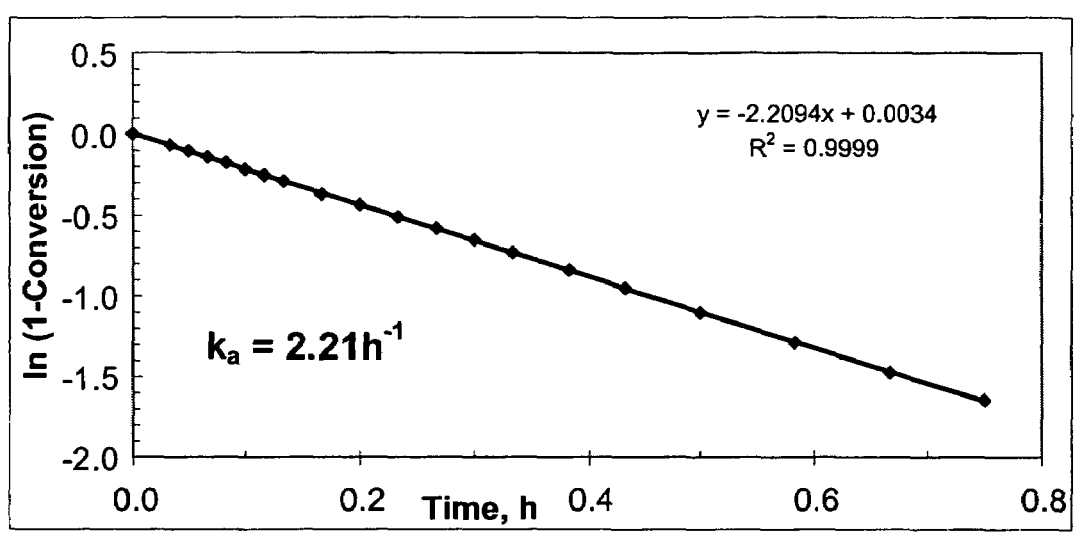
Figure 7:
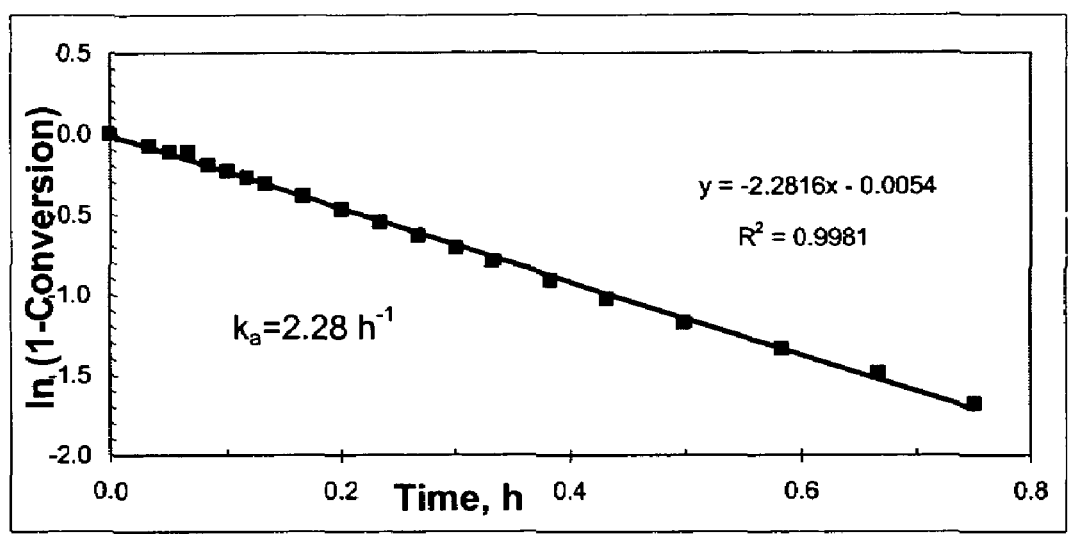

In the final products of the second test, 0.12 wt % of DME was measured by GC, proving that DME had not undergone any chemical reaction. The results which are shown in Tables 5 and 6 (and FIGS. 6 and 7) indicate that a high propylene content propylene feed obtained by the reaction of oxygenates to olefins and containing DME can be used with the associated benefits.

TABLE 5

Effect of dimethylether at 20 to 1 on Rh

| PRODUCT COMPOSITION | Wt % | g | moles |
|---|---|---|---|
| Propylene | 0.004 | 0.04 | 0.0010 |
| DME | 0.03 | 0.06 | 0.0014 |
| i-butanal | 0.42 | 0.88 | 0.0122 |
| n-butanal | 1.25 | 2.68 | 0.0371 |
| TPP | 10.25 | 21.42 | 0.0817 |
| TPPO | 0.14 | 0.29 | 0.0011 |
| Butyric acid | 0.08 | 0.17 | 0.0019 |
| TEGDE | 87.81 | 183.52 | 0.8256 |
| C3 in off gas | | 0.003 | 0.0001 |
| Substrate conversion | 99.46% molar | | |
| DME/Rh | 19.8 molar | | |

| time, min | DELTA P | Conversion | 1-conversion | ln(1-conv) |
|---|---|---|---|---|
| 0 | 0.000 | 0.000 | 1.000 | 0.000 |
| 2 | 0.600 | 6.501 | 0.935 | −0.067 |
| 3 | 0.920 | 9.968 | 0.900 | −0.105 |
| 4 | 1.240 | 13.435 | 0.866 | −0.144 |
| 5 | 1.510 | 16.360 | 0.836 | −0.179 |
| 6 | 1.810 | 19.610 | 0.804 | −0.218 |
| 7 | 2.080 | 22.535 | 0.775 | −0.255 |
| 8 | 2.330 | 25.244 | 0.748 | −0.291 |
| 10 | 2.870 | 31.094 | 0.689 | −0.372 |
| 12 | 3.270 | 35.428 | 0.646 | −0.437 |
| 14 | 3.700 | 40.087 | 0.599 | −0.512 |
| 16 | 4.080 | 44.204 | 0.558 | −0.583 |
| 18 | 4.430 | 47.996 | 0.520 | −0.654 |
| 20 | 4.800 | 52.005 | 0.480 | −0.734 |
| 23 | 5.250 | 56.880 | 0.431 | −0.841 |
| 26 | 5.670 | 61.431 | 0.386 | −0.953 |
| 30 | 6.170 | 66.848 | 0.332 | −1.104 |
| 35 | 6.690 | 72.482 | 0.275 | −1.290 |
| 40 | 7.120 | 77.140 | 0.229 | −1.476 |
| 45 | 7.450 | 80.716 | 0.193 | −1.646 |
| 50 | 7.750 | 83.966 | 0.160 | −1.830 |
| 55 | 7.960 | 86.241 | 0.138 | −1.983 |
| 60 | 8.150 | 88.300 | 0.117 | −2.146 |
| 90 | 8.780 | 95.125 | 0.049 | −3.021 |
| 120 | 8.980 | 97.292 | 0.027 | −3.609 |
| 180 | 9.180 | 99.459 | 0.005 | −5.220 |

TABLE 6

Effect of dimethylether at 82 to 1 on Rh

| PRODUCT COMPOSITION | Wt % | g | moles |
|---|---|---|---|
| Propylene | 0.009 | 0.105 | 0.0025 |
| DME | 0.12 | 0.274 | 0.0060 |
| i-butanal | 0.30 | 0.632 | 0.0088 |
| n-butanal | 1.14 | 2.402 | 0.0333 |
| TPP | 10.14 | 21.281 | 0.0812 |
| TPPO | 0.21 | 0.485 | 0.0017 |
| Butyric acid | 0.03 | 0.000 | 0.0000 |
| Tegde | 88.03 | 185.500 | 0.8345 |
| C3 in off gas |  | 0.006 | 0.0001 |
| Substrate conversion | 98.80% molar | | |
| DME/Rh | 81.6 molar | | |

| time, min | DELTA P | Conversion | 1-conversion | ln(1-conv) |
|---|---|---|---|---|
| 0 | 0.000 | 0.000 | 1.000 | 0.000 |
| 2 | 0.570 | 7.122 | 0.929 | −0.074 |
| 3 | 0.850 | 10.621 | 0.894 | −0.112 |
| 4 | 0.830 | 10.371 | 0.896 | −0.109 |
| 5 | 1.390 | 17.368 | 0.826 | −0.191 |
| 6 | 1.640 | 20.492 | 0.795 | −0.229 |
| 7 | 1.880 | 23.491 | 0.765 | −0.268 |
| 8 | 2.120 | 26.490 | 0.735 | −0.308 |
| 10 | 2.550 | 31.862 | 0.681 | −0.384 |
| 12 | 2.990 | 37.360 | 0.626 | −0.468 |
| 14 | 3.370 | 42.108 | 0.579 | −0.547 |
| 16 | 3.740 | 46.732 | 0.533 | −0.630 |
| 18 | 4.070 | 50.855 | 0.491 | −0.710 |
| 20 | 4.370 | 54.603 | 0.454 | −0.790 |
| 23 | 4.780 | 59.726 | 0.403 | −0.909 |
| 26 | 5.130 | 64.100 | 0.359 | −1.024 |
| 30 | 5.520 | 68.973 | 0.310 | −1.170 |
| 35 | 5.900 | 73.721 | 0.263 | −1.336 |
| 40 | 6.200 | 77.469 | 0.225 | −1.490 |
| 45 | 6.510 | 81.343 | 0.187 | −1.679 |
| 50 | 6.710 | 83.842 | 0.162 | −1.823 |
| 55 | 6.900 | 86.216 | 0.138 | −1.982 |
| 60 | 7.050 | 88.090 | 0.119 | −2.128 |
| 90 | 7.550 | 94.338 | 0.057 | −2.871 |
| 120 | 7.850 | 98.086 | 0.019 | −3.956 |
| 180 | 7.900 | 98.711 | 0.013 | −4.351 |

The invention claimed is:

1. A method of making a hydroformylated product comprising: (i) contacting an oxygenate with a molecular sieve catalyst to form an olefin composition comprising propylene; (ii) separating a propylene containing stream from the olefin composition and (iii) contacting said propylene containing stream with a rhodium hydroformylation catalyst and hydroformylating to form a hydroformylation product, wherein said propylene containing stream in steps (ii) and (iii) is characterized as comprising dimethyl ether in the amount of between 250 ppm and 5000 ppm.

2. The method according to claim 1 wherein the propylene containing stream contains at least 50 wt % propylene, not greater than 10 ppb by weight of sulfur calculated on an atomic basis, and at least 100 ppb by weight of dimethyl ether.

3. The method according to claim 1 wherein the propylene containing stream contains at least 60 wt % propylene.

4. The method according to claim 3, wherein the propylene containing stream contains at least 96 wt % propylene.

5. The method according to claim 1, comprising contacting the propylene containing stream with the rhodium hydroformylation catalyst at a pressure of from 0.05 to 50 MPag.

6. The method according to claim 1 further comprising hydrogenating an aldehyde from the hydroformylation product to manufacture an alcohol selected from the group consisting of normal butanol and isobutanol.

7. The method according to claim 1 further comprising oxidizing an aldehyde from the hydroformylation product to manufacture an acid selected from the group consisting of n-butyric and isobutyric acid.

8. The method according to claim 1 further comprising aldolizing an aldehyde from the hydroformylation product to form an aldol dimer and hydrogenating the aldol dimer to form a saturated alcohol.

9. The method according to claim 8 further comprising esterifying the saturated alcohol to manufacture an ester.

10. The method according to claim 9 wherein the ester is a phthalate ester.

11. The method according to claim 6 in which the hydrogenation reaction is rhodium catalysed.

12. The method according to claim 1, wherein the propylene containing stream in step (iii) further comprises propane and dimethyl ether.

13. The method according to claim 1, the improvement characterized by the absence of a step of distillation of dimethyl ether.

14. The method according to claim 1, the improvement characterized by the absence of a step of distillation of propane.

* * * * *